United States Patent
Sukovic et al.

(10) Patent No.: US 7,224,764 B2
(45) Date of Patent: May 29, 2007

(54) STAND-UP CT SCANNER

(75) Inventors: Predrag Sukovic, Birmingham, MI (US); Neal Clinthorne, Ann Arbor, MI (US)

(73) Assignee: Xoran Technologies, Inc., Ann Arbor, MI (US)

( * ) Notice: Subject to any disclaimer, the term of this patent is extended or adjusted under 35 U.S.C. 154(b) by 21 days.

(21) Appl. No.: 10/914,630

(22) Filed: Aug. 9, 2004

(65) Prior Publication Data

US 2005/0053186 A1    Mar. 10, 2005

Related U.S. Application Data

(60) Provisional application No. 60/493,289, filed on Aug. 7, 2003.

(51) Int. Cl.
 *G01N 23/083* (2006.01)
 *H05G 1/02* (2006.01)
(52) U.S. Cl. .................. 378/19; 378/20; 378/196
(58) Field of Classification Search ............... 378/15, 378/17, 20, 19, 196
 See application file for complete search history.

(56) References Cited

U.S. PATENT DOCUMENTS

| | | | | |
|---|---|---|---|---|
| 4,316,091 A | * | 2/1982 | Bernardi | 378/17 |
| 4,811,372 A | * | 3/1989 | Doebert et al. | 378/39 |
| 4,829,549 A | * | 5/1989 | Vogel et al. | 378/55 |
| 4,961,208 A | * | 10/1990 | Okada | 378/18 |
| 5,042,487 A | * | 8/1991 | Marquardt | 600/425 |
| 5,357,429 A | * | 10/1994 | Levy | 378/17 |
| 5,574,763 A | * | 11/1996 | Dehner | 378/17 |
| 6,178,220 B1 | * | 1/2001 | Freundlich et al. | 378/4 |
| 6,400,791 B1 | * | 6/2002 | Schwarz | 378/17 |
| 6,470,068 B2 | * | 10/2002 | Cheng | 378/20 |
| 6,735,274 B1 | * | 5/2004 | Zahavi et al. | 378/15 |
| 6,940,941 B2 | * | 9/2005 | Gregerson et al. | 378/4 |
| 2005/0053185 A1 | * | 3/2005 | Sukovic et al. | 378/4 |

OTHER PUBLICATIONS

"Stand-Up MRI", FONAR Corporation, 110 Marcus Drive, Melville, NY 11747.

* cited by examiner

*Primary Examiner*—Edward J. Glick
*Assistant Examiner*—Thomas R. Artman
(74) *Attorney, Agent, or Firm*—Carlson, Gaskey & Olds

(57) ABSTRACT

A CT scanner according to the present invention is particularly useful for scanning the spine and extremities, such as knees, and ankles, especially while the patient is in an upright position. The CT scanner generally includes a source and detector that are rotatable about a generally upright axis. The source and detector are also moved along the upright axis during rotation to perform a helical scan. The source and detector are mounted to an inner ring, which is rotatably mounted within an outer ring. The outer ring is fixedly mounted to a carriage that is movable along an upright rail.

10 Claims, 2 Drawing Sheets

STAND-UP CT SCANNER

This application claims priority to U.S. Provisional Application Ser. No. 60/493,289 filed Aug. 7, 2003.

BACKGROUND OF THE INVENTION

This invention relates generally to CT scanners and more particularly to a CT scanner that is particularly useful for scanning the spine and extremities, such as knees, and ankles, especially while the patient is in an upright position.

Conventional CT scanners require the patient to be horizontal. The scan cannot be obtained while the patient is in a standing position. As a result, for a patient who only experiences back (or hip or knee etc) pain while standing, the doctor cannot analyze the actual conditions under which the patient is experiencing pain (or other symptoms).

SUMMARY OF THE INVENTION

A CT scanner according to the present invention is particularly useful for scanning the spine and extremities, such as knees, and ankles, especially while the patient is in an upright position. The CT scanner generally includes a source and detector that are rotatable about a generally upright axis. The source and detector are also moved along the upright axis during rotation to perform a helical scan. The source and detector are mounted to an inner ring, which is rotatably mounted within an outer ring. The outer ring is fixedly mounted to a carriage that is movable along an upright rail.

In operation, the patient stands within the inner ring. The inner ring, outer ring and carriage move along the upright rail, while the inner ring rotates within the outer ring. In this manner, the source and detector are moved along helical paths to perform a helical scan. Thus, the CT scan can be performed on a standing patient.

The rail may be reconfigurable, e.g. bent to a curve or such that one portion of the rail is not parallel to another portion of the rail. The carriage follows the rail and performs a CT scan along that path. In this manner, the patient may be scanned in a bent position, which maybe the position that causes discomfort or problems.

BRIEF DESCRIPTION OF THE DRAWINGS

Other advantages of the present invention can be understood by reference to the following detailed description when considered in connection with the accompanying drawings wherein.

DETAILED DESCRIPTION OF THE PREFERRED EMBODIMENTS

Figure 1:
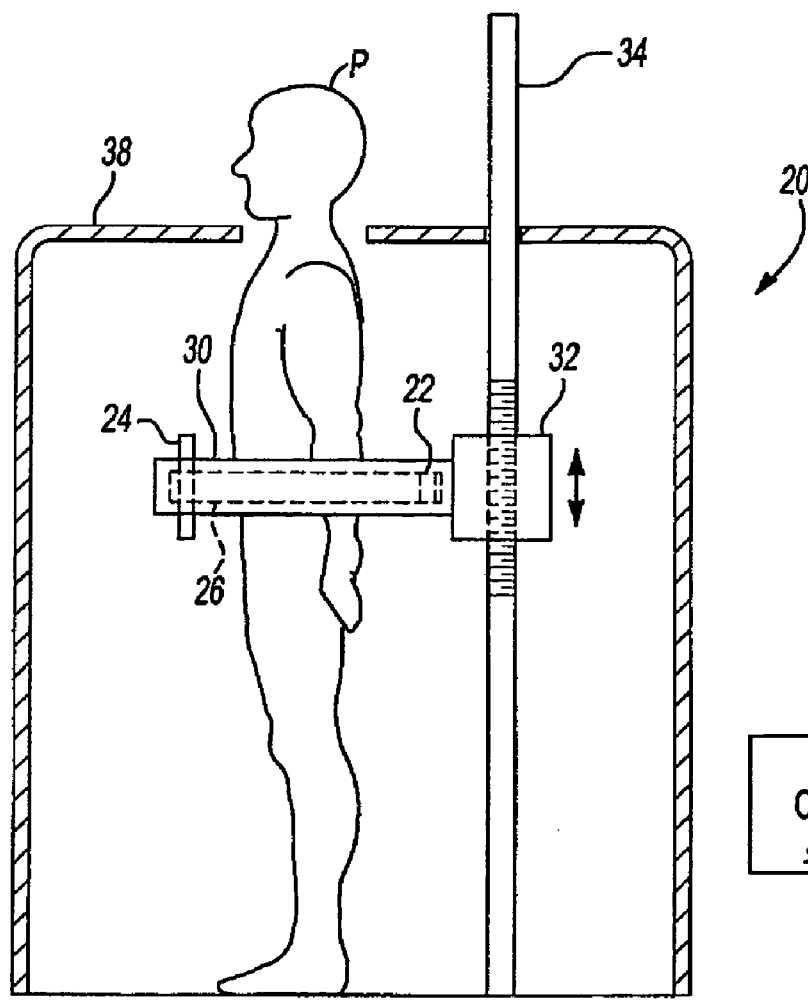
FIG. 1 is a plan view of a CT scanning system according to the present invention.
Figure 2:
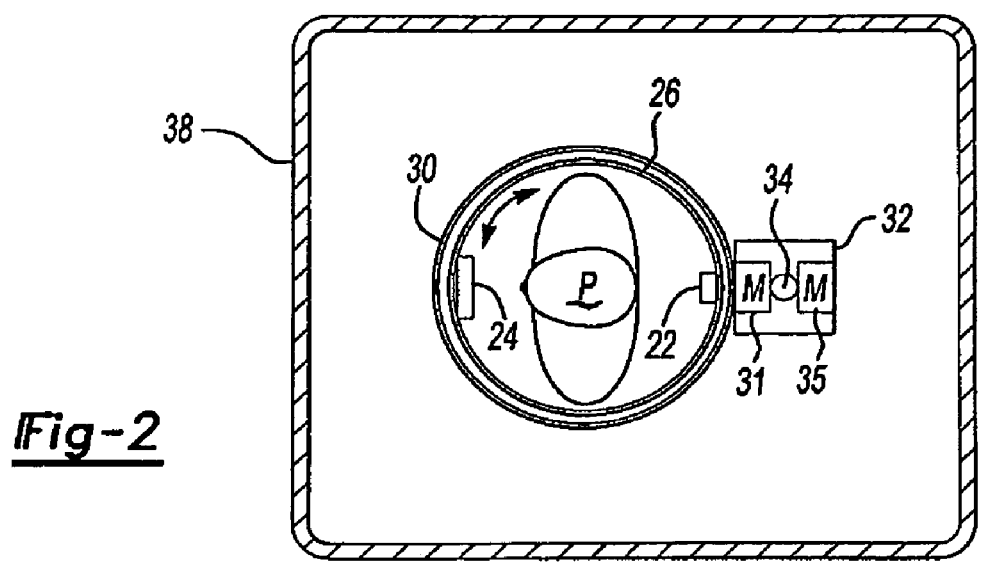
FIG. 2 is a side view of the CT scanning system of FIG. 1.
Figures 3, 4, 5, 6:
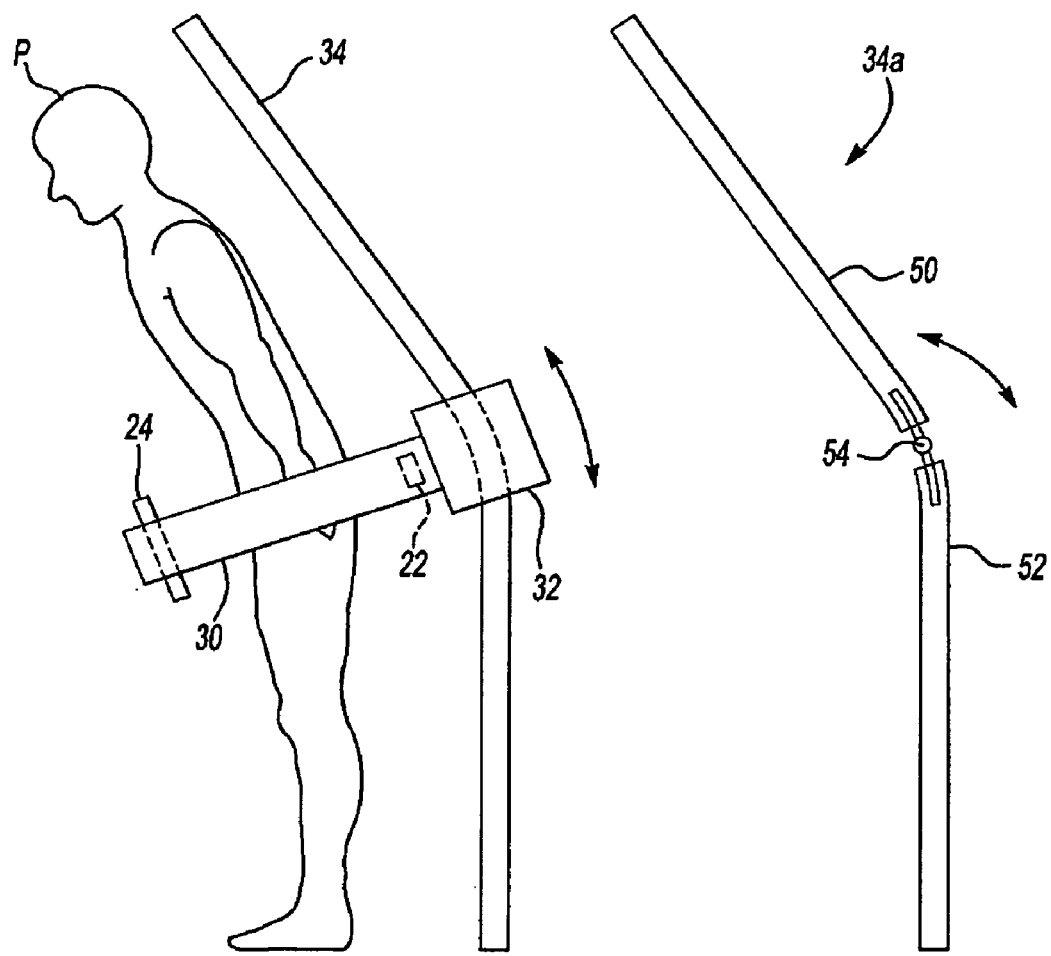
FIG. 3 shows the CT scanning system of FIG. 1, with the rail reconfigured to a bent position.
FIG. 4 shows an alternate reconfigurable rail.
FIG. 5 shows one possible detail of the rail of FIGS. 1-4.
FIG. 6 shows another possible detail of the rail of FIGS. 1-4.

A CT scanning system 20 according to the present invention is shown in FIGS. 1-3. Referring to FIGS. 1 and 2, the CT scanning system 20 includes an x-ray source 22 and detector 24 that are mounted on diametrically opposing inner surfaces of an inner ring 26 (or spiral). The source 22 is preferably a cone-beam x-ray source 22. The inner ring 26 is rotatably mounted within an outer ring 30. The angular position of the inner ring 26 relative to the outer ring 30 is changed and controlled by at least one motor 31 in a carriage 32, which supports the outer ring 30. The carriage 32, along with the inner and outer rings 26, 30, is mounted on a generally vertical rail 34. At least one motor 35 in the carriage 32 drives the carriage 32 up and down the rail 34 in a controlled manner. The rail 34 may be threaded or notched to facilitate the controlled travel of the carriage 32.

The operation of the above devices is controlled by a suitably programmed CPU 36, which may also perform the image storage and image processing necessary for the CT scans. The system 20 may optionally includes a radiation shield 38 substantially enclosing the patient P, the source 22 and the detector 24, but permitting the patient's head to be outside the shield 38. In this manner, the technicians may be able to stay in the room with the patient P during the scanning without receiving unnecessary radiation doses.

In use, the patient P stands upright within the rings 26, 30. The technician chooses an area to be scanned (e.g., knees, spine, hip, etc) and indicates the vertical starting and ending points for the scan to the CPU 36. The inner ring 26 then rotates within the outer ring 30 while the carriage 32 lifts (or lowers) the rings 26, 30 vertically along rail 34. In this manner, the source 22 and detector 24 move in a spiral, taking multiple x-ray images in known positions and orientations. The CPU 36 then develops a three-dimensional model of the scanned area of the patient using a reconstruction algorithm based upon the multiple x-ray images.

Referring to FIG. 3, the rail 34 is preferably selectively reconfigurable to create alternate paths for the rings 26, 30, source 22 and detector 24. For example, as shown, the rail 34 is preferably bendable or pivotable at a mid-point so that the scan of the patient P can be taken while the patient P is in bent position. Therefore, a scan of the patient P in the exact position that causes pain or other symptoms can be obtained.

Alternatively, the rail 34a may comprise several selectively lockable, pivoting components 50, 52 connected by a joint 54 to provide the ability to reconfigure the rail 34 to a plurality of paths for the scan to follow or any mechanical device that could provide a reconfigurable path for the carriage 32 to follow. Multiple rails 34 could also be used. Alternatively, a computer-controlled robot arm could be used to move the carriage 32 and rings 26, 30 along any path that could be set by the technician.

As indicated, the rail 34 may be threaded, as shown in FIG. 5, in order to facilitate movement by the carriage 32 (FIGS. 1-3). The motor 35 in the carriage 32 could rotatably drive a threaded member relative to the threads on rail 34 to cause relative translation. Alternatively, the rail 34b could be notched as shown in FIG. 6 to facilitate controlled translation by the motor 35 in the carriage 32 (FIGS. 1-3).

A variation of this invention includes advance image reconstruction methods, such as statistical image reconstruction methods (Penalized Weighted Least Squares, Maximum Likelihood, etc. . . . ) that would allow lower dosages to be used while still providing images of acceptable quality. Further, since one is interested only in the spine and not in the surrounding organs, one can collimate the X-ray source in such a way that only the spine (and a minimum of the surrounding area) is imaged. While this would generate 'truncated' data that would lead to some artifacts in the images the images would still be of sufficient quality for spine imaging. This is particularly true because the spine is such high contrast object relative to the background that the artifacts are not going to affect it as much as they would while trying to image softer tissue.

By using the above ideas to reduce the dosage of the scans, the scanner can be used to obtain the scans of the patient in several different positions (standing, bending over, etc. . . . ) to really assess the dynamics of the spine/extremity and improve the diagnosis.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:

1. A CT scanner comprising:
   a generally upright rail;
   a carriage movable along the rail;
   a motor mounted to drive the carriage along the rail;
   an outer ring mounted to the carriage;
   an inner ring rotatably mounted within the outer ring, wherein the inner ring and outer ring are cantilevered from the rail;
   an x-ray source mounted to the inner ring; and
   an x-ray detector mounted opposite the source and rotatable with the source.

2. The CT scanner of claim 1 further including a motor rotatably driving the inner ring relative to the outer ring.

3. The CT scanner of claim 1 wherein the rail is vertical.

4. The CT scanner of claim 1 wherein the x-ray source is a cone-beam x-ray source.

5. The CT scanner of claim 1 wherein the x-ray source is a cone-beam x-ray source.

6. The CT scanner of claim 1 further her including a radiation shield enclosing the x-ray source and the x-ray detector and including an upper opening through which a patient's head can extend.

7. The CT scanner of claim 1 wherein the rail extends through the carriage.

8. A CT scanner comprising:
   a generally upright rail, wherein the rail is reconfigurable such that one portion of the rail is not parallel to another portion of the rail;
   a carriage movable along the rail;
   an x-ray source rotatably mounted to the carriage; and
   an x-ray detector mounted opposite the source and rotatable with the source.

9. A method for generating an image of a patient including the steps of:
   a) positioning a patient upright between an x-ray source and a detector;
   b) rotating the source and the detector generally about the patient;
   c) translating the source and detector along a first path and then along a second path not parallel to the first path; and
   d) during said step b), taking an x-ray image at each of a plurality of rotational positions.

10. The method of claim 9 wherein the source and detector are translated vertically along the first path.

* * * * *

UNITED STATES PATENT AND TRADEMARK OFFICE
CERTIFICATE OF CORRECTION

PATENT NO. : 7,224,764 B2 Page 1 of 1
APPLICATION NO. : 10/914630
DATED : May 29, 2007
INVENTOR(S) : Sukovic et al.

It is certified that error appears in the above-identified patent and that said Letters Patent is hereby corrected as shown below:

Column 4, line 3: delete "her"

Signed and Sealed this

Seventh Day of August, 2007

JON W. DUDAS
*Director of the United States Patent and Trademark Office*